United States Patent [19]
Wadsworth et al.

[11] Patent Number: 5,453,620
[45] Date of Patent: Sep. 26, 1995

[54] NONDISPERSIVE INFRARED GAS ANALYZER AND GAS SAMPLE CHAMBER USED THEREIN

[75] Inventors: Mark V. Wadsworth, Richardson, Tex.; Julie G. Whitney, Georgetown, Ky.; William L. McCardel, Plano, Tex.

[73] Assignee: Texas Instruments Incorporated, Dallas, Tex.

[21] Appl. No.: 289,809

[22] Filed: Aug. 12, 1994

[51] Int. Cl.⁶ .................................................. G01N 21/61
[52] U.S. Cl. ............................................ 250/343; 356/440
[58] Field of Search .................................... 250/343, 345, 250/346, 349; 356/437, 440

[56] References Cited

U.S. PATENT DOCUMENTS

| | | | |
|---|---|---|---|
| 3,699,339 | 10/1972 | Taczak, Jr. | 250/353 |
| 3,920,336 | 11/1975 | Sackett | 356/440 |
| 4,709,150 | 11/1987 | Burough et al. | 250/338.5 |
| 5,026,992 | 6/1991 | Wong | 250/343 |
| 5,146,283 | 9/1992 | Parnoff et al. | 356/440 |
| 5,163,332 | 11/1992 | Wong | 73/863.23 |
| 5,222,389 | 6/1993 | Wong | 356/437 |
| 5,254,858 | 10/1993 | Wolfman et al. | 250/349 |

Primary Examiner—Carolyn E. Fields
Attorney, Agent, or Firm—Russell E. Baumann; Richard L. Donaldson; René E. Grossman

[57] ABSTRACT

A nondispersive infrared gas analyzer 10 for indicating the concentration of a selected gas uses a source of radiation 12 to supply radiation to a gas sample chamber 14. The gas chamber 14 functions as an optical channel for transmitting radiation from the source of radiation 12 to both a gas sensing detector 22 and reference detector 24. An inner surface 36 of the gas chamber 14 is an optical reflective surface for the chamber and has a constantly changing irregular profile to greatly enhance optical scattering of the radiation falling on it to provide an uniform disperse radiation output to the detectors 22, 24. Additionally, the source of radiation 12 is chosen to provide radiation which is defocused to further help in attaining homogenous radiation output from the gas sample chamber 14 to the detectors 22, 24.

16 Claims, 2 Drawing Sheets

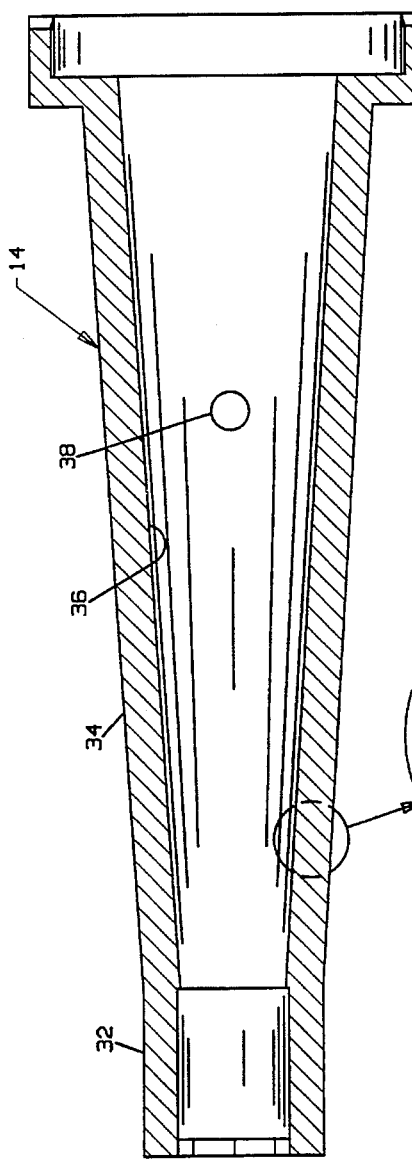
FIG. 3
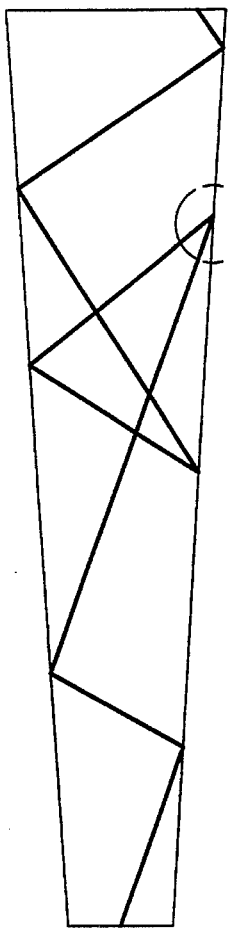
FIG. 4
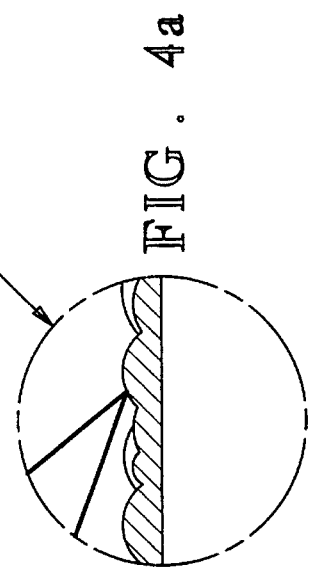
FIG. 4a
FIG. 3a

NONDISPERSIVE INFRARED GAS ANALYZER AND GAS SAMPLE CHAMBER USED THEREIN

FIELD OF THE INVENTION

The present invention relates to the field of gas analyzers; and more specifically, to gas analyzers of the type know as NDIR (nondispersive infrared) gas analyzers and the sample chamber used therein.

BACKGROUND OF THE INVENTION

It has been known in the prior art to use NDIR technology for gas analyzers due to the performance of such analyzers to be highly specific, sensitive and reliable. These gas analyzers use an optical waveguide or chamber containing the gas to be measured positioned between a light source and a detector. The light emitted from the light source travels through the chamber, and the gas contained therein, until it reaches the detector element for indicating gas concentrate levels. The major drawback of the past NDIR gas measurement devices has been their expense and complexity.

One attempt to overcome these difficulties with NDIR devices has been to use a diffusion-type gas chamber. U.S. Pat. No. 4,709,150 to Burough et al. issued Nov. 24, 1987 discloses such a device using a porous material tube for the gas sample chamber. Such a chamber allows the gas to be measured to flow through the porous walls. Another example as disclosed in U.S. Pat. No. 5,163,332 to Wong issued Nov. 17, 1992 uses a gas chamber with filtered apertures contained therein, and a highly specularly reflective inner surface. The use of this diffusion-type chamber eliminates the need for expensive optics, mechanical choppers and a gas supply and discharge means for adding to and taking away sample gas from the chamber.

These analyzers with the diffusion-type gas chamber, however, still suffer from generally high cost and complexity as well as reliability difficulties such as drift problems caused by variations in light source intensity and variations in environmental conditions such as ambient temperature.

SUMMARY OF THE INVENTION

Accordingly, it is an object of the present invention to provide an improved NDIR gas analyzer which solves the drift problems caused by environmental and operational variations.

It is another object of the present invention to provide an NDIR gas analyzer which is compact in size, reliable in operation and economical to produce.

In accordance with one aspect of the present invention, an improved NDIR gas analyzer uses a reference channel with additional detector to accurately reflect changes in environmental and operational parameters.

In accordance with another aspect of the invention, an improved NDIR gas analyzer uses a common signal and optical gas chamber for both gas channel and reference channel in which radiation is scattered in the chamber in a uniform manner to both a gas detector and a reference detector to allow for accurate compensation for changes in environmental and operational parameters.

In accordance with still another aspect of this invention, an improved NDIR analyzer; and specifically the gas sample chamber used therein, requires no special complex filtering system for the gas to be analyzed.

In accordance with yet still another aspect of this invention, an improved gas sample chamber with an optical reflective surface with a constantly changing profile is provided to greatly enhance optical scattering of radiation falling on the optical surface.

Briefly described, the gas analyzer of the present invention comprises a nondispersive infrared gas analyzer for indicating the concentration of a selected gas comprising a source of radiation, a gas sample chamber adapted to receive gas and positioned to receive radiation from said source of radiation, said gas sample chamber of a generally elongated tube shape with two ends, a hollow central area, and an outer wall having an inner and outer surface, said inner surface of the outer wall acting as an optical reflective surface for radiation from said source comprising a plurality of distinct raised portions of a varying height from an average plane of the surface of the outer wall surface so as to produce a homogeneous, dispersed distribution of radiation from the source through the gas sample chamber, and detector means for producing a signal representative of the concentration of the selected gas having at least one gas sensor and a reference sensor, said sensors each receiving the same radiation in the absence of said selected gas to be analyzed.

BRIEF DESCRIPTION OF THE DRAWINGS

Other objects, advantages and details of the invention appear in the following detailed description of proposed embodiments of the invention, the detailed description referring to the drawings in which:

FIG. 3 is a cross-section view of a gas sample chamber of a gas analyzer in accordance with the present invention;

FIG. 3a is an enlarged view of a portion of the surface of an inner wall of the gas chamber of FIG. 3;

FIG. 4 diagrammatically shows a typical radiation ray trace of radiation in a gas sample chamber in accordance with the present invention; and FIG. 4a is an enlarged view of a portion of FIG. 4.

DETAILED DESCRIPTION OF THE PREFERRED EMBODIMENT

Figure 1:
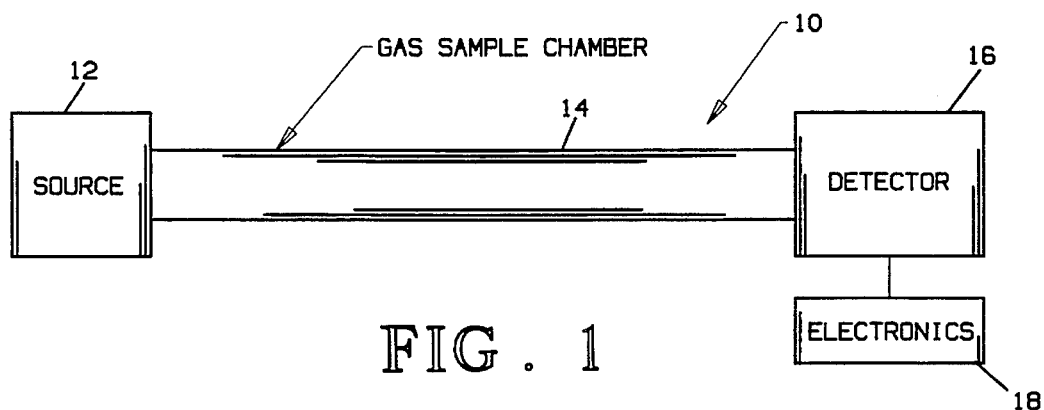
FIG. 1 is a side elevational view showing the major components of a gas analyzer in accordance with the present invention.

As shown in FIG. 1, a gas analyzer 10 of the present invention includes a source of radiation 12, a gas chamber 14 and a detector means 16. The detector means 16 produces an electrical signal that represents the intensity of the radiation falling on it. This electrical signal is applied to an electronic circuit 18 that converts it to a signal that represents the concentration of the gas to be measured. Electrical circuits of this type are well known in the art such a circuit using a substraction algorithm or a division algorithm.

In accordance with this invention, the source of radiation 12 is typically a small incandescent lamp that produces visible light and infrared radiation, and is positioned at one end of the gas chamber 14. A preferred source is a hot tungsten filament lamp placed in a parabolic reflector. It has been found to be particularly useful if the parabolic reflector is "defocused" to produce a ring of high intensity radiation in a generally doughnut shape instead of being focused from one point. That is, the radiation from the source is preferably directed so as to best ensure contact with the chamber inner wall, and not transverse the chamber without reflecting one or more times off the wall of the chamber. This feature allows for the use of a chamber of shorter length and aids in the formation of a homogeneous radiation output delivered to the detectors along with the design of the gas chamber 14 which is discussed in further detail below.

Figure 2:
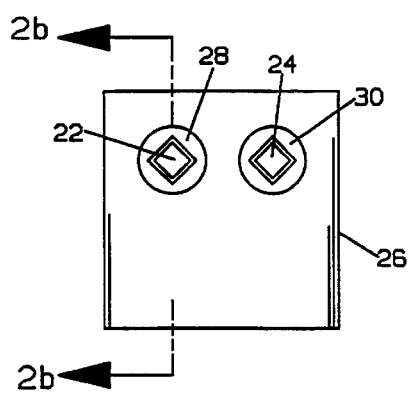
FIG. 2 is a front elevational view showing a detector means of a gas analyzer in accordance with the present invention.
Figure 2A:
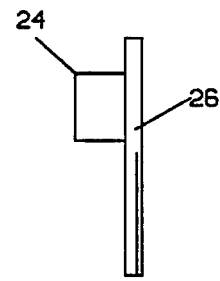
FIG. 2a is a side elevational view of FIG. 2.
Figure 2B:
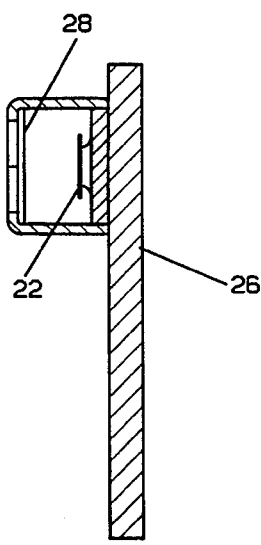
FIG. 2b is a cross-sectional view cut along line 2b—2b of FIG. 2.

In accordance with this invention, the detector means 16 as shown in FIG. 2, has at least one sensing detector 22 and a reference detector 24 mounted on the surface of a substrate 26 such as a printed circuit board. This printed circuit board with detectors is positioned at any desired location in the optical path of the radiation from the source, but it is important that the sensing detector and the reference detector see the same radiation in the absence of the selected gas to be analyzed. One preferred design would have detectors 22, 24 positioned at the one end of gas chamber 14 adjacent each other opposite the end of the chamber containing radiation source 12. The detector members 22, 24 convert heat/light energy into an electric signal by changing capacitance or resistive properties, and should be as identical as possible. It has been found advantageous to use a pyroelectric type detector such as a 405 model made by Eltec Instruments. Associated with each gas sensing detector (for indicating the presence of the gas to be detected) is a narrow pass band filter 28 (see FIG. 2c) placed in front of the detector in the optical path between the source and detector so that the detector receives mainly radiation of a wave length that is strongly absorbed by the gas whose presence and/or concentration is to be determined. Associated with the reference detector 24 is a different narrow pass band filter 30 preferably with a center pass band close to that of the filter used with the sensing detector 22. This filter is not to be affected by the presence of gas detected by detector 22, and with detector 24 is used to be able to cancel the effects caused by variation in source intensity as well as variations in environmental conditions such as ambient temperature. This means that reference detector 24 with filter 30 must see or track the same background signal that gas detector 22 with filter 28 sees to be totally effective. The detectors 22, 24 supply a signal to electrical circuit 18.

In accordance with this invention, gas chamber 14 as shown in FIG. 3 has a generally tubular shape being open at both ends with a hollow center area. It has been found desirable to have a conical shaped tubular gas chamber 14 to increase the homogenation of the radiation signal supplied to detector means 16 by providing a greater variety of possible incident angles as the radiation travels along the chamber and to provide greater room for positioning sensors 22, 24. Gas chamber 14 has an outer wall 32 with an outer surface 34 and an inner optically reflective surface 36. Typically, the outer wall has a generally constant wall thickness except as provided by a textured inner wall surface as discussed below. Such a chamber can be economically produced by joining two halves of an injection molded polymeric material such as Acrylonitrile Butadiene Styrene (ABS) to form the tubular shape. There is no need to specifically seal these halves when joining them together or to generally be concerned with a sealed device. Typically, one or more apertures 38 are provided in gas chamber outer wall 32 to allow for the ingress and egress of gas to the gas chamber. No special complex filtering system is needed to be used in the apertures 38.

As mentioned above, inner surface 36 of gas chamber 14 serves as the reflective optical surface for the gas analyzer 10 from the radiation source 12 to the detector means 16. This chamber optical surface provides the function as the common reflective surface from the common light source to both the gas sensing detector 22 and the reference detector 24 for the gas analyzer. This means that a sensing channel functionally includes radiation source 12, inner optical surface 36 and gas detector 22 with filter 28 and a reference channel functionally includes radiation source 12, inner optical surface 36 and reference detector 24 with filter 30. There is no need for a separate optical reflective surface (waveguide) for the gas sensing channel and the reference channel; and in fact, it is desirable to use the same chamber to provide a uniform disperse radiation to the detectors.

A further requirement of inner optical reflective surface 36 in the present invention is that the surface has a constantly changing irregular profile to greatly enhance optical scattering of radiation falling on the optical surface. Such a surface is preferably a continuously curved (textured) surface with a plurality of joined raised features or portions 40 of varying heights (see FIG. 3a) from the surface of the inner surface of the outer wall of the gas chamber. This surface will provide that radiation from source 12 transversing the chamber will not have the same, or nearly the same, angle of reflections as measured from the normal to the outside wall surface 34 of the chamber as a specularly reflective surface would provide (see FIGS. 4 and 4a). Consequently, this surface is not adapted to produce nondistorted image reproduction, and in fact, will provide for a dispersed totally distorted image/radiation output to the detectors. This feature is very important when using a reference channel/detector to assure that the gas detector and reference detector "see" the same background radiation.

In practice, for radiation in the 2 to 5 micron range, the plurality of features generally need to have a height of 0.010 to 0.030 of an inch from the base surface of the inner wall to the top of the surface of the feature and an average feature size (when viewed looking toward the surface of the outer wall at a normal direction) of 0.02 to 0.13 of an inch. This feature, height and size will vary for different lengths of radiation; and thus, will be preselected for the particular gas to be measured. Such a textured optical surface can be easily put into the mold used to produce the tubular gas chamber by etching techniques. It is preferred that this textured surface is metalized (not shown) as is known in the art with a metal such as aluminum which in turn can be coated with a thin polymer coating such as polyethylene to protect against oxidation.

It should be noted that although preferred embodiments of the invention have been described by way of illustrating the invention, the invention includes all modifications and equivalents of the disclosed embodiments falling within the scope of the appended claims.

We claim:

1. A nondispersive infrared gas analyzer for indicating the concentration of a selected gas comprising a source of radiation, a gas sample chamber adapted to receive gas and positioned to receive radiation from said source of radiation, said gas sample chamber of a generally elongated tube shape with two ends, a hollow central area, and an outer wall having an inner and outer surface, said inner surface of the outer wall acting as an optical reflective surface for the radiation from said source comprising a plurality of distinct raised portions of varying height from an average planar surface of the outer surface of the outer wall so as to produce a homogeneous, dispersed distribution of radiation from the source through the gas sample chamber, and detector means for producing a signal representative of the concentration of the selected gas having at least one gas sensing detector and a reference detector, said detectors each receiving the same radiation in the absence of said selected gas to be analyzed.

2. A gas analyzer as set forth in claim 1 wherein said plurality of distinct raised portions are set at preselected varying heights depending on the selected gas to be analyzed.

3. A gas analyzer as set forth in claim 1 wherein said detector means includes one gas sensing detector and a first narrow pass band filter placed in front of said gas sensing detector between the source of radiation and the gas sensing detector, so that the gas sensing detector receives mainly radiation of a wave length that is strongly absorbed by said selected gas, and a second narrow pass band filter for the reference detector with a different center pass band from that of the first narrow pass band filter and not affected by said selected gas.

4. A gas analyzer of claim 3 wherein said second narrow pass band filter has a center pass band close to that of first narrow pass band filter.

5. A gas analyzer of claim 1 where said source of radiation produces defocused radiation to best ensure contact with said optical reflective surface of the inner surface of the outer wall of the gas chamber.

6. A gas analyzer of claim 5 wherein said source of radiation is a hot tungsten filament lamp placed in a parabolic reflector.

7. A gas analyzer of claim 1 further including an electrical circuit to convert the signals from the detectors to a signal representative of the concentration of the selected gas.

8. The gas analyzer of claim 7 wherein said electric circuit receives input from both said at least one gas sensing detector and said reference detector.

9. A gas analyzer of claim 1 wherein said gas sample chamber includes at least one aperture to allow for ingress and egress of gas into the gas chamber.

10. A gas analyzer of claim 1 wherein the optical reflective surface of said gas sample chamber serves as a common reflective surface from the radiation source to the at least one gas sensing detector and to the reference detector.

11. A gas analyzer of claim 1 wherein said gas sample chamber is of a generally elongated conical tube shape.

12. A gas sensor chamber for transmitting radiation through gases present in the chamber to a detector means comprising an elongated tube with two ends, a hollow center area, and an outer wall having an inner and outer surface, said inner surface of the outer wall acting as an optical reflective surface for the gas sample chamber and having a constantly changing irregular profile which provides for desired optical reflection while greatly enhancing optical scattering of the radiation falling on the optical reflective surface so as to produce a homogeneous, dispersed distribution of the radiation to said detector means.

13. A gas sample chamber of claim 12 wherein said constantly changing irregular profile of said optical reflector surface is provided by a plurality of distinct raised portions of varying height from the average planar surface of the outer surface of the outer wall.

14. A gas sample chamber of claim 13 wherein said plurality of distinct raised portions are set at preselected varying heights depending on the gases present in the chamber.

15. A gas sample chamber of claim 12 further including at least one aperture to allow for ingress and egress of gas into the gas sample chamber.

16. A gas sample chamber of claim 12 wherein said elongated tube is conical in shape.

* * * * *